(12) United States Patent
Lee

(10) Patent No.: US 10,022,147 B2
(45) Date of Patent: Jul. 17, 2018

(54) STATIC POINTING DEVICE APPLICATOR

(71) Applicant: Choon Kee Lee, Denver, CO (US)

(72) Inventor: Choon Kee Lee, Denver, CO (US)

( * ) Notice: Subject to any disclaimer, the term of this patent is extended or adjusted under 35 U.S.C. 154(b) by 513 days.

(21) Appl. No.: 14/935,419

(22) Filed: Nov. 8, 2015

(65) Prior Publication Data

US 2017/0128098 A1   May 11, 2017

(51) Int. Cl.
*A61B 17/34* (2006.01)
*A61B 8/08* (2006.01)
*A61B 8/00* (2006.01)

(52) U.S. Cl.
CPC ........ *A61B 17/3403* (2013.01); *A61B 8/0841* (2013.01); *A61B 8/40* (2013.01); *A61B 8/4209* (2013.01); *A61B 8/4455* (2013.01); *A61B 2017/3405* (2013.01); *A61B 2017/3413* (2013.01)

(58) Field of Classification Search
CPC ........ A61B 17/3403; A61B 2017/3407; A61B 8/42; A61B 8/4272; A61B 8/4281
See application file for complete search history.

(56) References Cited

U.S. PATENT DOCUMENTS

| | | | |
|---|---|---|---|
| 4,646,754 A * | 3/1987 | Seale | A61B 3/16 600/402 |
| 5,623,931 A | 4/1997 | Wung | |
| 5,855,558 A * | 1/1999 | Nakao | A61B 8/0833 600/459 |
| 5,941,889 A | 8/1999 | Cermak | |
| 6,203,499 B1 | 3/2001 | Imling | |
| 6,296,614 B1 * | 10/2001 | Pruter | A61B 17/3403 600/461 |
| 6,475,152 B1 | 11/2002 | Kelly, Jr. | |
| 6,485,426 B2 | 11/2002 | Sandhu | |
| 7,691,066 B2 | 4/2010 | Kosaku | |
| 7,846,103 B2 | 12/2010 | Cannon, Jr. | |
| 7,976,469 B2 | 7/2011 | Bonde | |
| 8,057,487 B2 | 11/2011 | Chu | |
| 8,073,592 B2 | 12/2011 | Cermak | |
| 8,118,743 B2 | 2/2012 | Park | |
| 8,216,149 B2 | 7/2012 | Oonuki | |
| 8,241,301 B2 | 8/2012 | Zhang | |
| 8,257,264 B2 | 9/2012 | Park | |

(Continued)

FOREIGN PATENT DOCUMENTS

CA  2285595 A1 * 10/1998
FR  2127372 A5 * 10/1972

(Continued)

OTHER PUBLICATIONS

EIC 3700 Search Report by Janice Burns.*
EIC 3700 Search Report by Fern Birtwistle.*

*Primary Examiner* — Patricia Park
*Assistant Examiner* — Nate S Sunwoo

(57) ABSTRACT

The present invention presents an applicator having a non-reusable static pointing device reversibly attachable to a face of an ultrasound transducer to attach the non-reusable static pointing device to the face of the ultrasound transducer in a consistent and accurate way. The static pointing device attached to the face of the ultrasound transducer is coupled with an ultrasound positioning apparatus and is to produce a linear shadow line in a visualized ultrasonographic field.

12 Claims, 8 Drawing Sheets

(56) References Cited

U.S. PATENT DOCUMENTS

| | | | |
|---|---|---|---|
| 8,409,099 B2 * | 4/2013 | Vitek | A61B 8/4281 |
| | | | 600/439 |
| 8,496,593 B2 | 7/2013 | Park | |
| 8,521,257 B2 | 8/2013 | Whitcomb | |
| 8,574,160 B2 | 11/2013 | Gorzitze | |
| 8,706,186 B2 | 4/2014 | Fichtinger | |
| 2012/0285250 A1 * | 11/2012 | Rhim | A61N 7/02 |
| | | | 73/632 |
| 2015/0201994 A1 * | 7/2015 | Vetter | A61B 18/149 |
| | | | 606/48 |
| 2015/0202010 A1 | 7/2015 | Lee | |
| 2015/0238265 A1 | 8/2015 | Lee | |

FOREIGN PATENT DOCUMENTS

| | | | |
|---|---|---|---|
| GB | 2130726 A | * | 6/1984 |
| JP | H076957 B2 | * | 1/1995 |
| JP | 8215195 A | * | 8/1996 |
| WO | WO2014172396 A2 | * | 10/2014 |

* cited by examiner

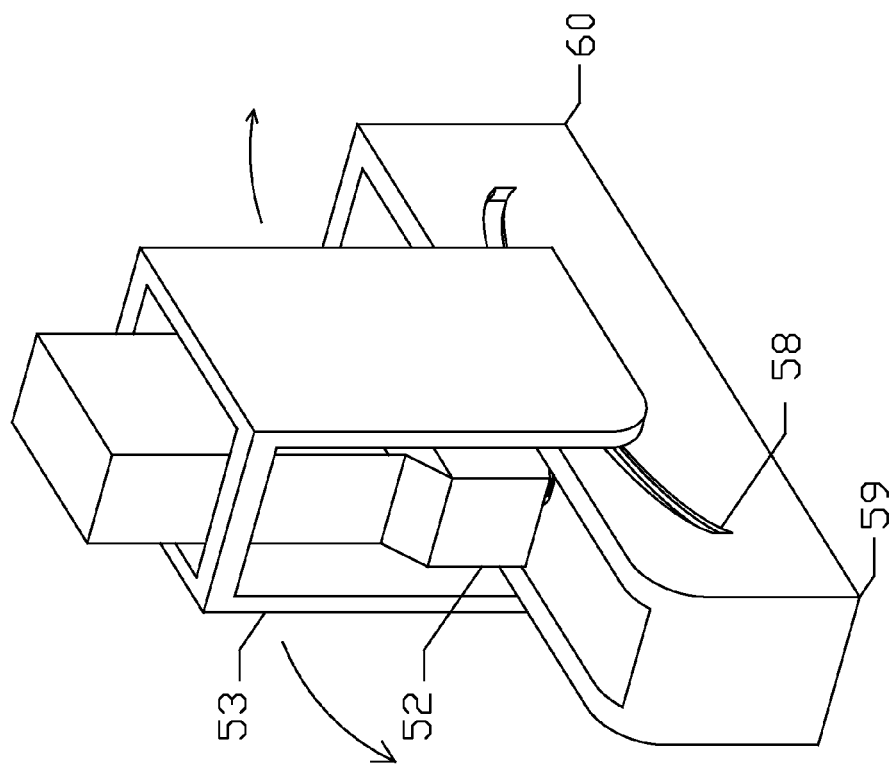
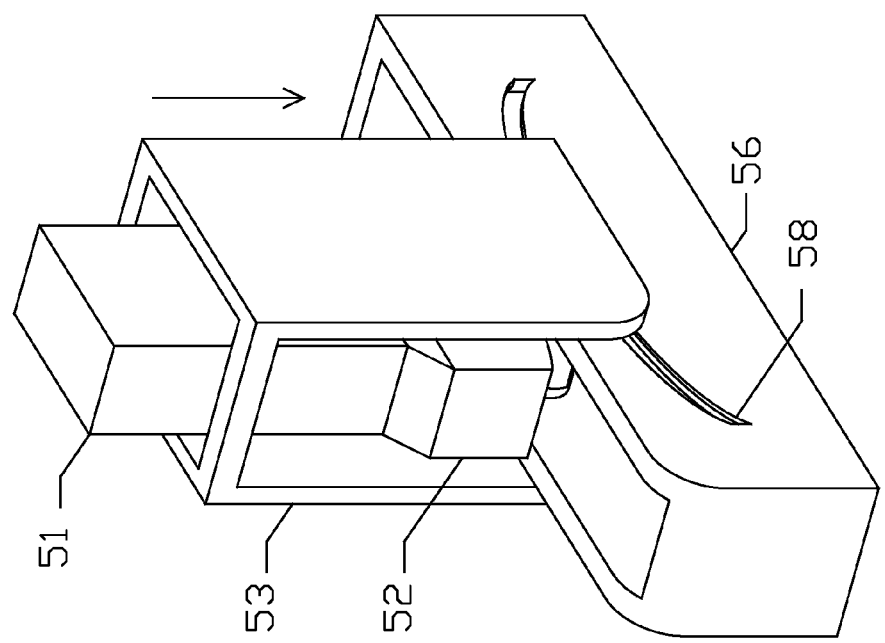

STATIC POINTING DEVICE APPLICATOR

CROSS REFERENCE TO RELATED APPLICATIONS

Attached please refer to the Information Disclosure Statement for the cross reference to related applications.

TECHNICAL FIELD

The present invention relates generally to the field of positioning guidance of insertion of invasive devices in a living body for medical purposes. More specifically, the present invention provides an applicator for an ultrasonographic pointing device to be reversibly attached to an ultrasound transducer.

BACKGROUND OF THE INVENTION

In the previous inventions of the utility patent applications of Ser. Nos. 14/097,228, 14/160,492, 14/187,285, 14/311,338, 14/321,958, 14/462,320, 14/511,150, and 14/527,736, I proposed that an invasive tubular device be guided by an ultrasound imaging that displays a visual reference axis crossing a tissue object, in an ultrasonographic view, which is a target of the invasive tubular device. In these inventions, a linear shadow line as a reference axis for an ultrasound positioning apparatus can be produced by either a movable pointer (Ser. Nos. 14/097,228, 14/160,492, 14/187,285, 14/311,338, 14/321,958, 14/511,150) or a static pointer (Ser. No. 14/527,736).

The prior invention of the utility patent application of Ser. No. 14/527,736 provides placement of a static pointing device in an enclosure attached to the ultrasound positioning apparatus and attachment of the static pointing device to a face of an ultrasound transducer. A permanent placement of the static pointing device to the face of an ultrasound transducer assures of correct positioning of a pointer of the static pointing device in relation to the ultrasound transducer, without variability, for accurate calculation of an angle and a depth of an invasive tubular device to reach the tissue object. Yet, the permanent attachment of the static pointing device would limit availability of the ultrasound positioning apparatus only to compatible and paired ultrasound transducers with the ultrasound positioning apparatus. On the other hand, attachment of a non-reusable static pointing device to a face of an ultrasound transducer manually by a user each time the ultrasonographic positioning apparatus is used is more complicated than the permanent attachment, in that a degree of accuracy of the manual attachment of the non-reusable static pointing device is inherently variable and greatly affects accuracy of the ultrasonographic calculation of the angle and depth of the invasive tubular device to reach the tissue object.

In an effort to broaden availability of ultrasonographic imaging guidance for invasive biopsy procedures, to accommodate general stand-alone ultrasound transducers for the ultrasound positioning apparatus of the prior inventions and to maintain consistent accuracy of the attachment of the non-reusable static pointing device to the face of the ultrasound transducer, the present invention provides an applicator having a non-reusable static pointing device that can be reversibly attachable to the face of the ultrasound transducer, which guarantees accurate application of the non-reusable static pointing device to the face of the ultrasound transducer. The applicator of the present invention releasably encloses the non-reusable static pointing device, and is configured to releasably house a proximal portion of the ultrasound transducer and to rotatably attach the non-reusable static pointing device to the face of the ultrasound transducer. The static pointing device of the present invention uses a thin ultrasound-transmissible flexible polymer sheet that is bendable and has an adhesive on a surface of the sheet contacting the face of the ultrasound transducer for reversible attachment.

SUMMARY OF THE INVENTION

The present invention provides an applicator having a non-reusable static pointing device comprising a stationary linear pointer fixedly embedded in a thin ultrasound-transmissible flexible polymer sheet that can be reversibly attached to a face of an ultrasound transducer. The applicator is configured to releasably enclose a proximal portion of the ultrasound transducer, and comprises a rotatable drum around which the static pointing device reversibly and adherently wraps and a guiding mechanism for the proximal portion of the ultrasound transducer to attach the static pointing device to the face of the ultrasound transducer.

In one embodiment, the static pointing device is provided as one layer of sheet or stacked-up layers of sheet, and comprises one flexible polymer or a plurality of flexible polymers which are ultrasound-transmissible and the stationary linear pointer which is fixedly embedded in the polymer sheet and is not ultrasound-transmissible. The static pointing device is placed perpendicularly to and in front of the face of the ultrasound transducer and is to contact a skin overlying a tissue object. On a surface of the static pointing device contacting the face of the ultrasound transducer, a polymeric adhesive is applied for reversible attachment to the face of the ultrasound transducer. The static pointing device is configured as flexible to conform to either a flat or a curvilinear contour of the face of the ultrasound transducer and to cover an entire contact surface of the face. The stationary linear pointer runs in parallel with a linear axis of an ultrasound transducer array and is configured to block a portion of ultrasound waves emanating from the ultrasound transducer toward the tissue object.

In one embodiment, the stationary linear pointer is provided as a bendable, thin straight longitudinal bar which runs in parallel with a transverse axis of the static pointing device and the linear axis of the ultrasound transducer array. The stationary linear pointer is embedded in the single-layered polymeric sheet of the static pointing device or in one layer of polymeric sheet which is sandwiched between at least two layers of sheet. A transverse cross-section of the stationary linear pointer is configured in a box shape, a V shape or a semi-circular shape. An apex of the V shaped cross-section of the stationary linear pointer points to the skin and both open ends in cross section point to the face of the ultrasound transducer. Similarly, a convex portion of the semi-circular cross section points to the skin and both open ends in cross section point to the face of the ultrasound transducer. These configurations are to optimize blockade of ultrasound transmission emanating from the ultrasound transducer.

In one embodiment, the static pointing device is reversibly and circumferentially applied to an outer circumferential wall of a rotatable cylindrical drum in a way enveloping the outer wall of the rotatable cylindrical drum. A skin-facing surface of the static pointing device contacts internally the outer wall of the rotatable cylindrical drum and the adhesive surface of the static pointing device configured to adhere to the face of the ultrasound transducer is exposed externally. The rotatable cylindrical drum wrapped by the static pointing device is reversibly mountable on a pair of axial pins protruding from inner walls of an enclosure, and is made freely rotatable around a longitudinal axis of the rotatable cylindrical drum about the axial pins.

In one embodiment, the applicator is configured as a box-shaped enclosure which houses the rotatable cylindrical drum inside the enclosure and has a pair of longitudinal guide rail slots on an outer surface of both longitudinal vertical sidewalls of the box-shaped enclosure. A pivotable rectangular enclosure for the proximal portion of the ultrasound transducer is pivotably connected to the box-shaped enclosure in the pair of the longitudinal guide rail slots, which is pivotably foldable over the box-shaped enclosure and slidable inside the pair of the longitudinal guide rail slots. The box-shaped enclosure has an open upper part which is to accommodate the proximal part of the ultrasound transducer. The rotatable cylindrical drum is positioned on a pair of pins with each pin protruding from an inner surface of the longitudinal vertical sidewall of the box-shaped enclosure, in a way a longitudinal axis of the rotatable cylindrical drum aligns with a transverse axis of the box-shaped enclosure. A cylindrical end on each side of the rotatable cylindrical drum is configured with a central hole which is releasably inserted in the pin and allows the rotatable cylindrical drum to rotate freely about the pin. Each longitudinal guide rail slot of the box-shaped enclosure is configured as linear or curvilinear along a longitudinal axis of the box-shaped enclosure, which is made open on the outer surface of the longitudinal sidewall and is to be coupled with a wheel protruding from an inner wall of a distal end of the pivotable rectangular enclosure. The pivotable rectangular enclosure has an open proximal end through which the proximal part of the ultrasound transducer slides in and the distal end which is also open and pivotably anchored to the longitudinal guide rail slots of the box-shaped enclosure. The pivotable rectangular enclosure is configured to be reversibly folded up over the box-shaped enclosure and to be unfolded about the wheel of the distal end to a right angle to the longitudinal axis of the box-shaped enclosure. The pivotable rectangular enclosure in an unfolded configuration at the right angle to the box-shaped enclosure is configured to slide over the box-shaped enclosure along the longitudinal axis of the box-shaped enclosure back and forth by way of a pair of the wheels of the distal end sliding inside the longitudinal guide rail slots.

In one embodiment, a central transverse axial line of the distal end of the pivotable rectangular enclosure in an unfolded configuration at the right angle to the box-shaped enclosure is configured to align with a central longitudinal axial line located on the outer circumferential wall of the rotatable cylindrical drum. This alignment is achieved by a vertical notch protruding from the cylindrical end of the rotatable cylindrical drum on both sides, configured to slide in a corresponding vertical recess made on the inner surface of each vertical sidewall just above the pin of the box-shaped enclosure, and by an alignment of the wheel of the distal end of the pivotable rectangular enclosure with both the central transverse axial line of said distal end and the vertical notch of the cylindrical end of the rotatable cylindrical drum. The static pointing device is configured to have the stationary linear pointer be positioned along the central longitudinal axial line of the rotatable cylindrical drum.

In one embodiment, the stationary linear pointer is positioned in the polymeric sheet of the static pointing device in a way to circumferentially wrap around the outer wall of the rotatable cylindrical drum at a right angle to the central longitudinal axial line of the rotatable cylindrical drum. The position of the stationary linear pointer inside the polymeric sheet is at a mid point from both longitudinal ends of the static pointing device to align with a mid point of the central longitudinal axial line from both the cylindrical ends of the rotatable cylindrical drum.

In one embodiment, the longitudinal guide rail slots of the box-shaped enclosure is configured to have a bend spring at a pivoting junction with the wheels of the distal end of the pivotable rectangular enclosure in an unfolded configuration at the right angle to the box-shaped enclosure, which is configured to prevent sliding movement of the wheels of the pivotable rectangular enclosure inside the longitudinal guide rail slots unless the distal end of the pivotable rectangular enclosure is pushed vertically downward to get engaged with the longitudinal guide rail slots. A vertical distance of a push from a disengaged position of the distal end to a engaged position of the distal end corresponds to a vertical distance from the face of the proximal part of the ultrasound transducer to the outer circumferential wall of the rotatable cylindrical drum. Once the distal end of the pivotable rectangular enclosure is pushed in, and gets engaged with the longitudinal guide rail slots and slides inside said rail slots back and forth, the face of the proximal part of the ultrasound transducer glides over the adhesive surface of the sheet of the static pointing device which wraps around the rotatable cylindrical drum. The face of the proximal part of the ultrasound transducer is then covered by the static pointing device which adheres tightly to the face of the ultrasound transducer.

In one embodiment, the longitudinal guide rail slots of the box-shaped enclosure is configured as curvilinear along the longitudinal axis, which has a convex portion pointing upward and both ends of the guide rail slot pointing downward. The curvilinear configuration allows a convex face of an ultrasound transducer housed in the pivotable rectangular enclosure to glide on the rotatable cylindrical drum of the box-shaped enclosure while remaining equidistant over a curvilinear contour of the face of the ultrasound transducer between an axis of the curvilinear contour of the face of the ultrasound transducer and an axis of the rotatable cylindrical drum.

BRIEF DESCRIPTION OF THE DRAWINGS

FIG. 1A represents a flat ultrasound transducer head; FIG. 1B represents a flat static pointing device; FIG. 1C represents the position alignment assembly for the flat ultrasound transducer head; FIG. 1D represents a convex ultrasound transducer head; FIG. 1E shows a convex static pointing device; FIG. 1F shows the position alignment assembly for the convex ultrasound transducer head.

FIG. 2A shows the static pointing device applicator in a folded-up configuration; FIG. 2B shows the ultrasound transducer head; FIG. 2C shows a pivoted pivotable rectangular enclosure for the ultrasound transducer head at a right angle to a box-shaped enclosure of the static pointing device applicator.

FIG. 4A shows a stationary linear pointer embedded in the static pointing device along a central longitudinal axial line of the rotatable cylindrical drum and the rotatable cylindrical drum circumferentially wrapped by the static pointing device; FIG. 4B shows a stationary linear pointer embedded transversely at a mid point from both longitudinal ends of the static pointing device and the rotatable cylindrical drum.

FIG. 6A shows the curvilinear head of the ultrasound transducer; FIG. 6B shows a pivotable rectangular enclosure; FIG. 6C shows a convex static pointing device and a rotatable cylindrical drum; FIG. 6D shows a box-shaped enclosure with a curvilinear guide rail slot located on an outer surface of each vertical sidewall.

FIG. 7A shows a folded-up applicator which can be unfolded; FIG. 7B shows a pivoted pivotable rectangular enclosure at a right angle to a box-shaped enclosure, into which an ultrasound transducer head is inserted; FIG. 7C shows a push-down movement of the pivotable rectangular enclosure with the ultrasound transducer head; FIG. 7D shows a horizontal to and fro movement of the pivotable rectangular enclosure with the ultrasound transducer head along the linear guide rail slot of the box-shaped enclosure.

FIGS. 8A and 8B show a schematic example of a method of attaching the static pointing device to the curvilinear ultrasound transducer head: FIG. 8A shows placement of the curvilinear ultrasound transducer head in the pivotable rectangular enclosure pivoted at a right angle to the box-shaped enclosure having the curvilinear guide rail slots; FIG. 8B shows a to and fro curvilinear movement of both the ultrasound transducer and pivotable rectangular enclosure along the curvilinear guide rail slots of the box-shaped enclosure.

DETAILED DESCRIPTION OF THE DRAWINGS

As described below, the present invention provides a non-reusable static pointing device and an applicator for the static pointing device to be attached to a face of an ultrasound transducer head. It is to be understood that the descriptions are solely for the purposes of illustrating the present invention, and should not be understood in any way as restrictive or limited. Embodiments of the present invention are preferably depicted with reference to FIGS. 1 to 8, however, such reference is not intended to limit the present invention in any manner. The drawings do not represent actual dimension of devices, but illustrate the principles of the present invention.

Figure 1A:
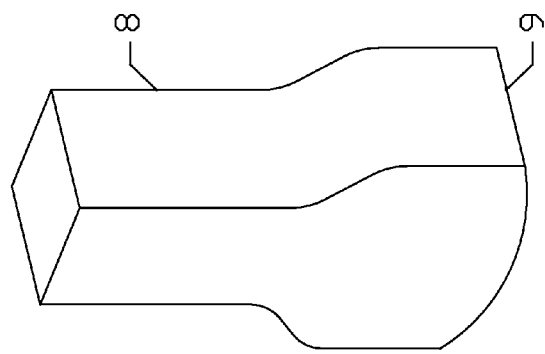
FIGS. 1A, 1B, 1C, 1D, 1E, and 1F show a schematic illustration of examples of an ultrasound transducer head, a static pointing device and a position alignment assembly.
Figure 1B:
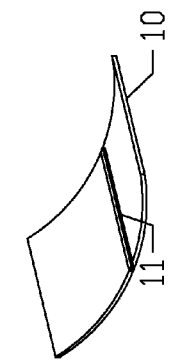
Figure 1C:
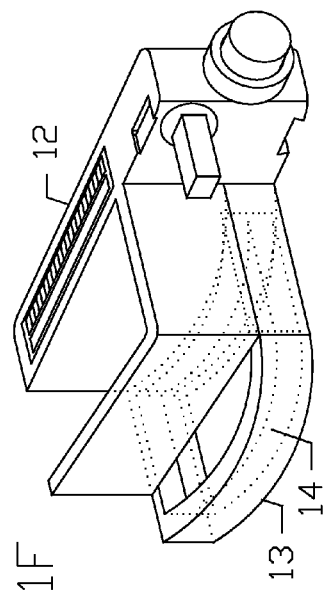
Figure 1D:
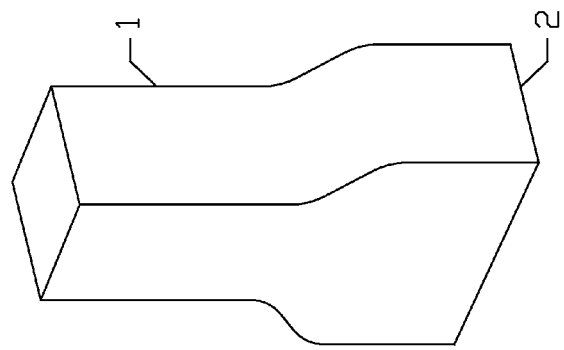
Figure 1E:
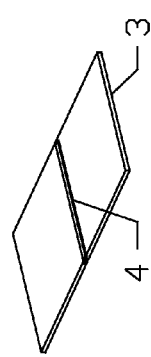
Figure 1F:
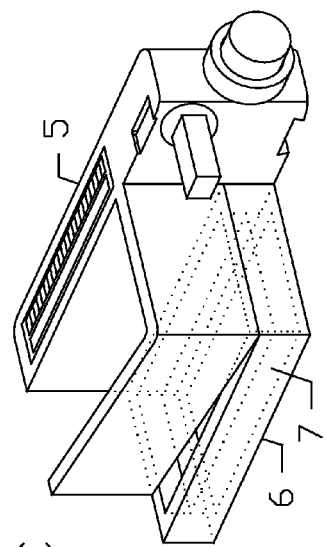

FIGS. 1A, 1B, 1C, 1D, 1E, and 1F show a schematic illustration of examples of an ultrasound transducer head, a static pointing device and a position alignment assembly. FIG. 1A represents an ultrasound transducer head 1 having a flat face 2 to contact with a skin of a patient. FIG. 1B represents a flat static pointing device 3 with a stationary linear pointer 4 embedded in the static pointing device 3 which can be attached to the flat face 2 of the ultrasound transducer of FIG. 1A. FIG. 1C represents the position alignment assembly 5 for the flat ultrasound transducer head. The position alignment assembly 5 has an enclosure 7 with a flat bottom 6 for the flat ultrasound transducer head. The position alignment assembly is configured to be used with an invasive tubular device of the prior inventions. FIG. 1D represents an ultrasound transducer head 8 with a convex face 9. FIG. 1E shows a convex static pointing device 10 with a stationary linear pointer 11 embedded in the static pointing device 10 which is configured to be attached to the convex face 9 of the ultrasound transducer head 8 of FIG. 1D. FIG. 1F shows the position alignment assembly 12 with an enclosure 14 of the ultrasound transducer head having a convex bottom 13 for the convex ultrasound transducer head.

Figure 2B:
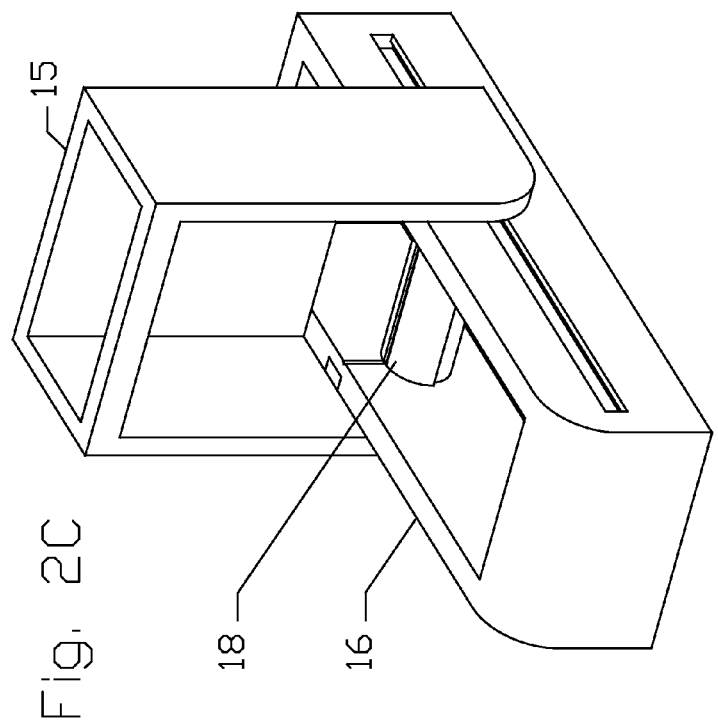
FIGS. 2A, 2B and 2C show a schematic example of a static pointing device applicator and an ultrasound transducer head.
Figure 2C:
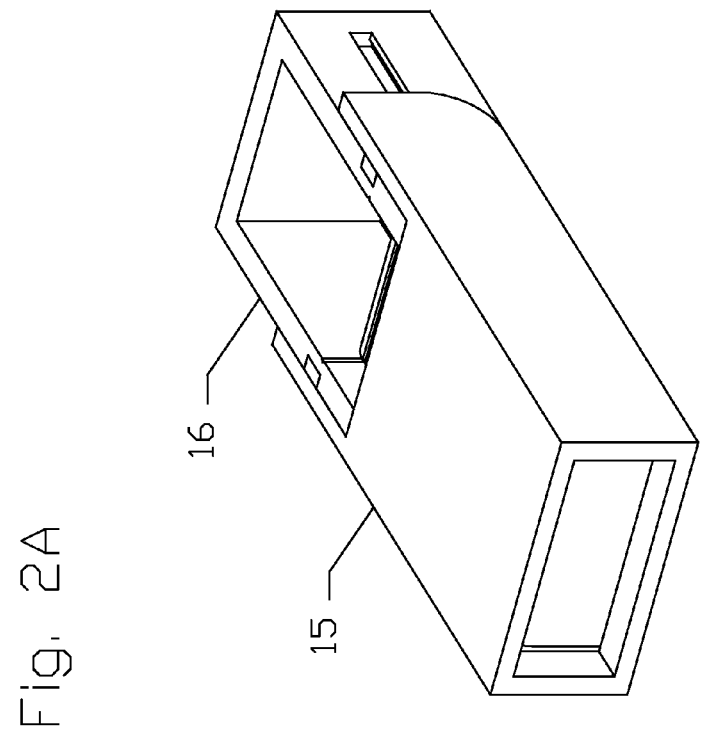
Figure 2A:
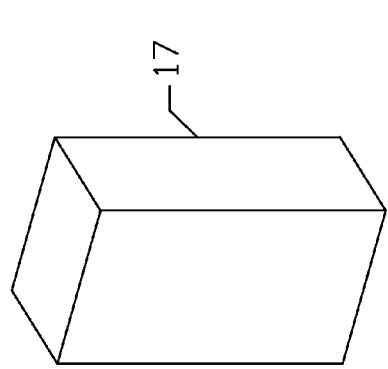

FIGS. 2A, 2B and 2C show a schematic example of a static pointing device applicator and an ultrasound transducer head. FIG. 2A shows a pivotable rectangular enclosure 15 folded up over a box-shaped enclosure 16 of the static pointing device applicator. FIG. 2B shows the ultrasound transducer head 17 which is to be releasably inserted in an open space of the pivotable rectangular enclosure 15 in an unfolded configuration at a right angle to the box-shaped enclosure 16 of FIG. 2C. A proximal end of the ultrasound transducer 17 is to contact with a static pointing device 18 releasably attached to an outer circumferential surface of a rotatable cylindrical drum.

Figure 3:
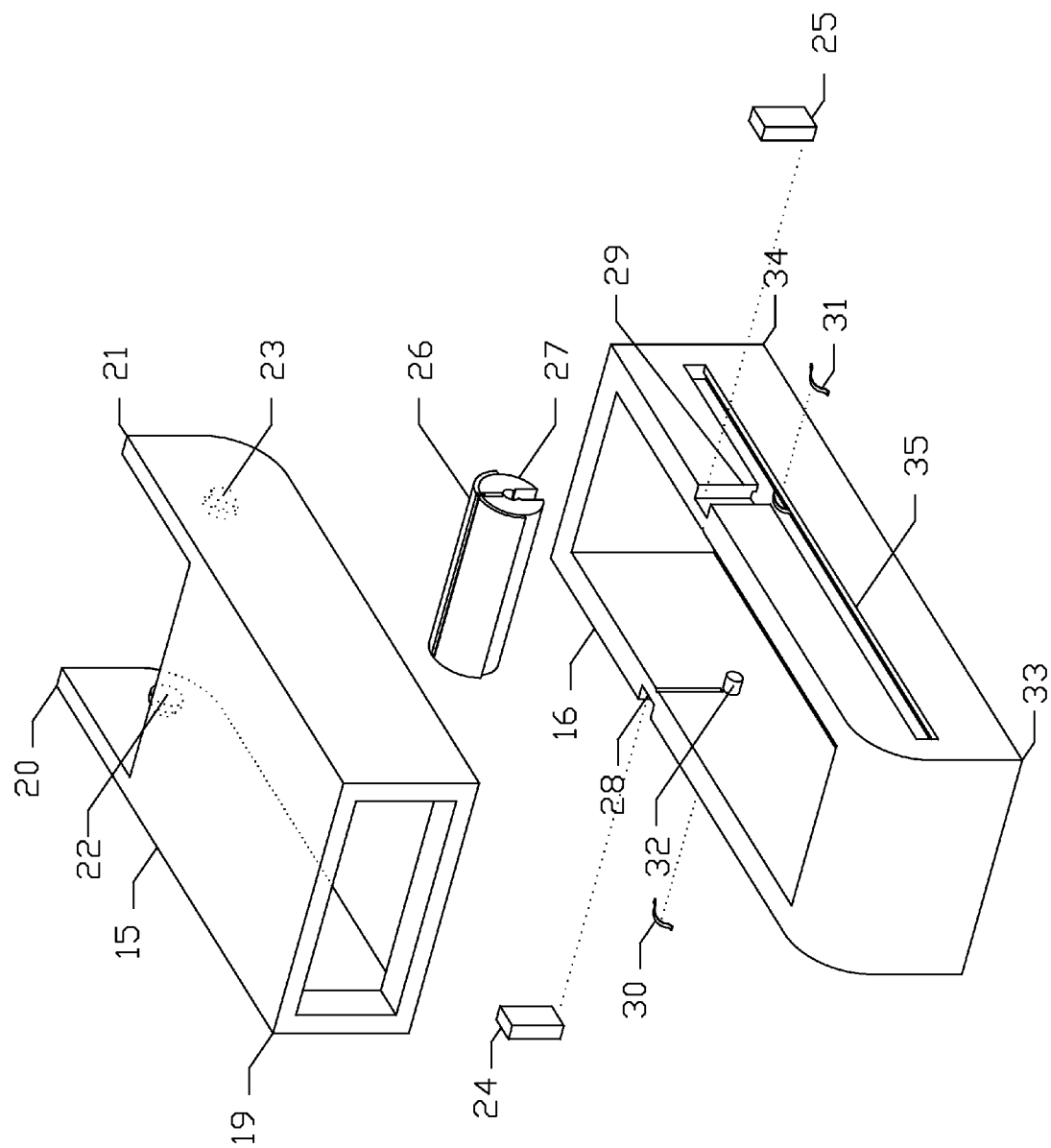
FIG. 3 shows an exploded view of a schematic example of the static pointing device applicator.

FIG. 3 shows an exploded view of a schematic example of the static pointing device applicator. The pivotable rectangular enclosure 15 has a proximal end 19 which is open to accommodate an ultrasound transducer head, a pair of distal ends 20 and 21 which extend distally for a length from a lateral sidewall on each side and a pair of pivotable wheels 22 and 23, located close to the distal ends, which protrude from an inner surface of the lateral sidewall on each side. The box-shaped enclosure 16 is open on an upper portion and has a closed proximal end 33 and a closed distal end 34. On an inner surface of a lateral vertical sidewall, there is provided a pin 32 which is inserted in a central hole of a rotatable cylindrical drum 27. A similar pin is located on the other inner wall of an opposite lateral vertical sidewall, which is not depicted in this view. The rotatable cylindrical drum 27 is releasably wrapped by a static pointing device 26. On an outer surface of the lateral vertical sidewall, there is provided a vertical slot 29 which allows the pivotable wheel 23 to slide in to a longitudinal guide rail slot 35. At a junction between the vertical slot 29 and the longitudinal guide rail slot 35, there is provided a bend spring 31 which prevents the pivotable wheel 23 from getting into the longitudinal guide rail slot 35 unless being pushed to flatten the bend spring 31 to allow engagement of the pivotable wheel 23 with the longitudinal guide rail slot 35. The vertical slot 29 is configured to be permanently sealed by a corresponding rectangular piece 25 following completion of assembly of the static pointing device applicator. Similarly, a vertical slot 28 of a pair of the vertical slots is depicted on an opposite lateral vertical sidewall along with a corresponding rectangular piece 24 and a bend spring 30. The vertical slot 28 is to be permanently sealed by the rectangular piece 24.

Figure 4A:
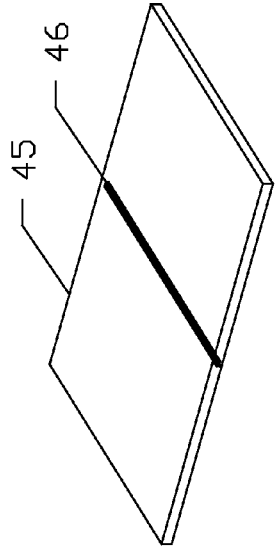
FIGS. 4A and 4B depict schematic examples of a rotatable cylindrical drum of the static pointing device applicator with a static pointing device.
Figure 4A:
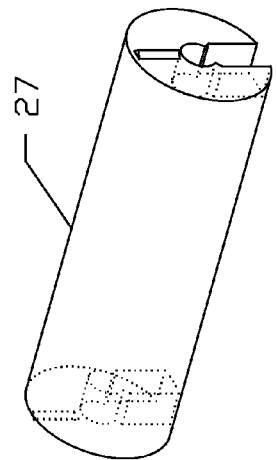
Figure 4A:
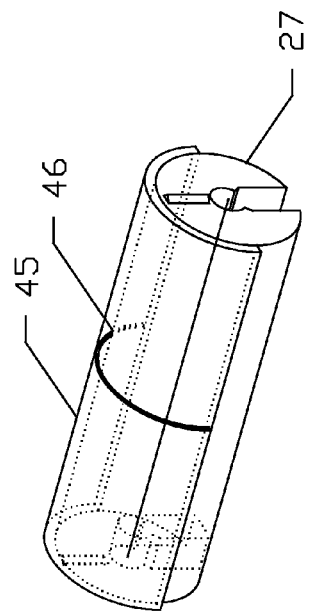
Figure 4B:
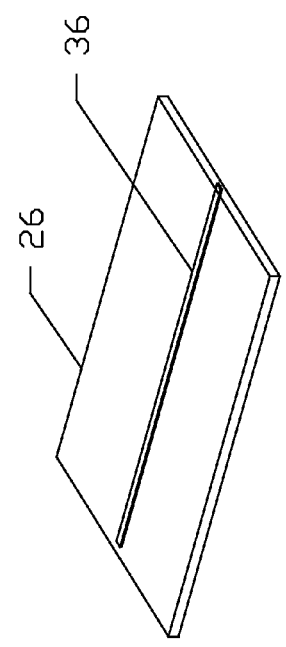
Figure 4B:
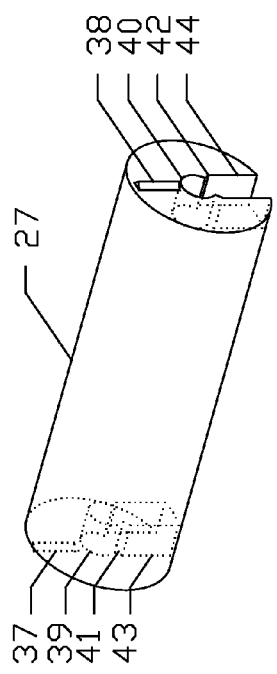
Figure 4B:
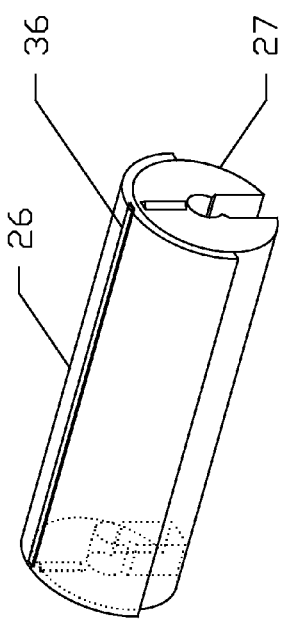

FIGS. 4A and 4B depict schematic examples of a static pointing device with an embedded stationary linear pointer. FIG. 4A shows a stationary linear pointer 36 embedded in a polymer sheet of a static pointing device 26 along a central longitudinal axial line of a rotatable cylindrical drum 27. On a cylindrical end of the rotatable cylindrical drum 27, there is provided a central hole 39 into which the pin 32 of the box-shaped enclosure depicted in FIG. 3 is releasably inserted. The central hole 39 is open to an outer circumferential wall through an open conduit 43 which allows the pin 32 of FIG. 3 to slide in to the central hole 39. On an opposite end of the rotatable cylindrical drum, a similar central hole 40 and an open conduit 44 are provided. Between the central hole 40 and the conduit 44, there is provided a ridge 42 which serves to reversibly lock the pin inside the central hole 40. On the other side, a similar ridge 41 is placed in between the central hole 39 and the conduit 43. Vertically above the central holes 39 and 40, a pair of vertically linear notches 37 and 38 protrude from each cylindrical end, which serves to position the static pointing device 26 inside the box-shaped enclosure in a way to align the stationary linear pointer 36 vertically up in a 12'o clock direction. The static pointing device 26 is releasably attached to the outer circumferential wall of the rotatable cylindrical drum 27 in a way the stationary linear pointer 36 aligns with a central longitudinal axial line of the rotatable cylindrical drum 27. FIG. 4B shows a stationary linear pointer 46 embedded transversely at a mid point from both longitudinal ends of a static pointing device 45 and from both the cylindrical ends of the rotatable cylindrical drum 27.

Figure 5:
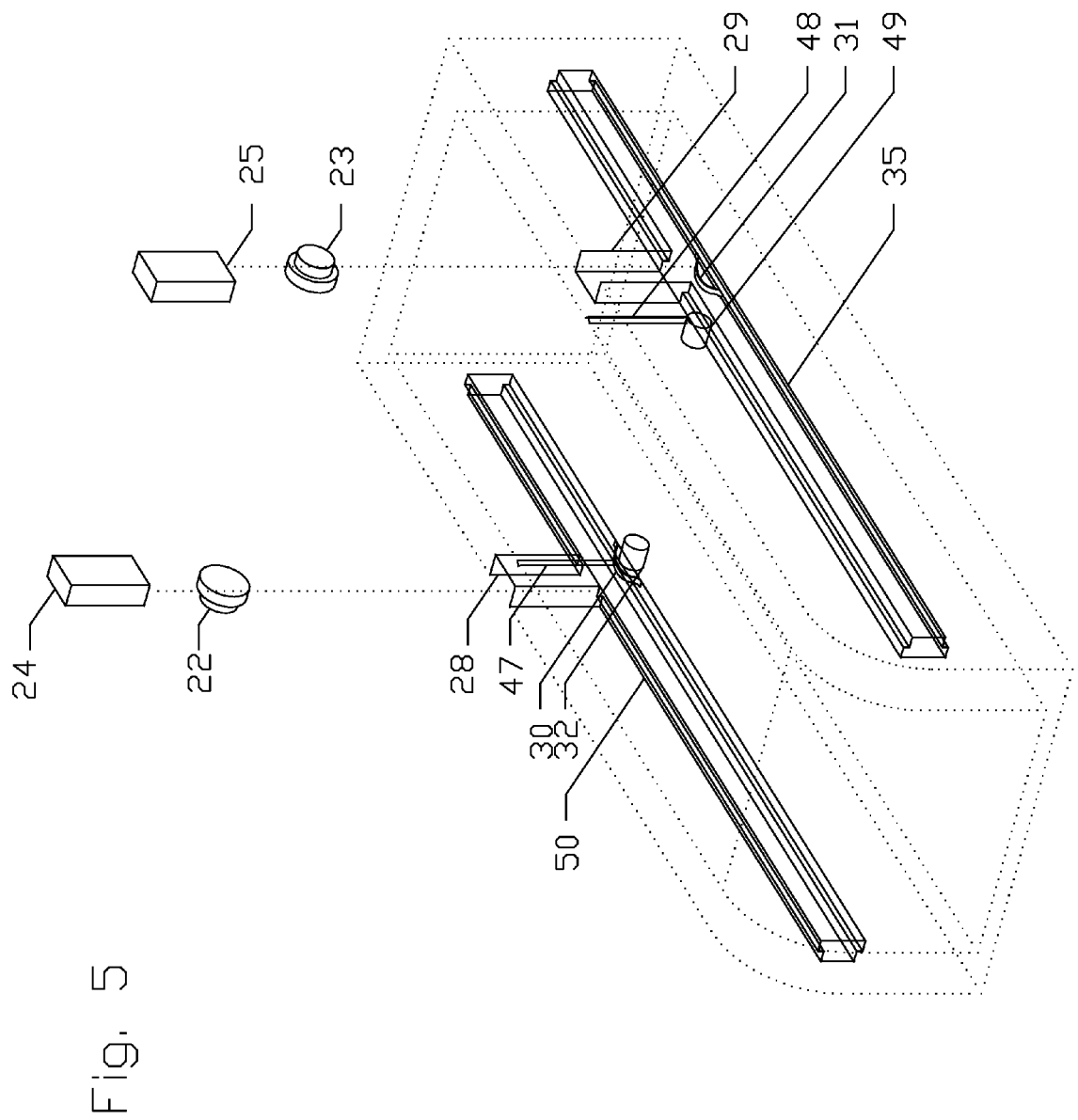
FIG. 5 illustrates a schematic see-through example of a configuration of the box-shaped enclosure having a longitudinal linear guide rail slot on an outer surface, and a centering recess and a pin on an inner surface of each vertical sidewall.

FIG. 5 illustrates a schematic see-through example of a configuration of the box-shaped enclosure having a pair of longitudinal guide rail slots 35 and 50 on an outer surface of the lateral vertical sidewalls, and a pair of the pins 32 and 49 protruding from an inner surface of the lateral vertical sidewalls. Vertically above each pin, a centering recess is provided to align the central axial line of the rotatable cylindrical drum 27 shown in FIG. 4A with the centering recess. The centering recess 47 is above the pin 32 and the other centering recess 48 is above the pin 49. Referring to FIG. 4A, the centering recess 47 mates with the vertical notch 37 and the centering recess 48 mates with the vertical notch 38 of the rotatable cylindrical drum 27. Referring to FIG. 3, the pivotable wheel 22 of the pivotable rectangular enclosure slides in the vertical slot 28 to the junction between the vertical slot 28 and the longitudinal guide rail slot 50, above the bend spring 30. On the opposite vertical sidewall, the pivotable wheel 23 of the pivotable rectangular enclosure slides in the vertical slot 29 to the junction between the vertical slot 29 and the longitudinal guide rail slot 35, above the bend spring 31. Once the pivotable wheels are in place, the vertical slots 28 and 29 are permanently sealed by the corresponding rectangular pieces 24 and 25 to lock in the pivotable rectangular enclosure to the box-shaped enclosure. The pivotable wheels 22 and 23 of the pivotable rectangular enclosure slide inside the longitudinal guide rail slots to provide a to and fro movement of the pivotable rectangular enclosure along the longitudinal axis of the box-shaped enclosure.

Figure 6A:
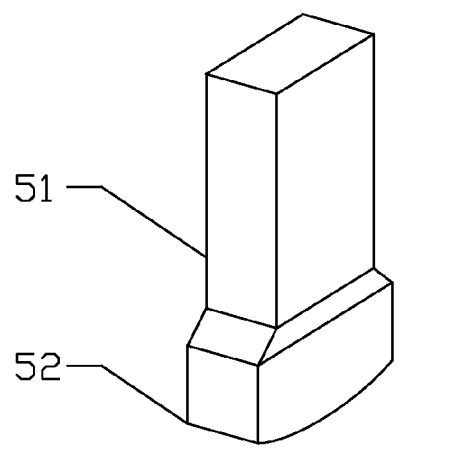
FIGS. 6A, 6B, 6C and 6D shows a schematic illustration of an example of a static pointing device applicator for a curvilinear head of an ultrasound transducer.
Figure 6B:
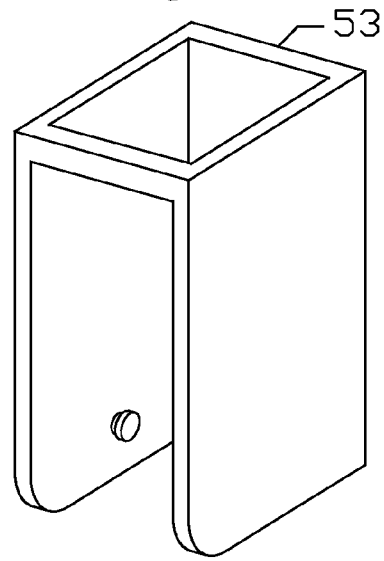
Figure 6C:
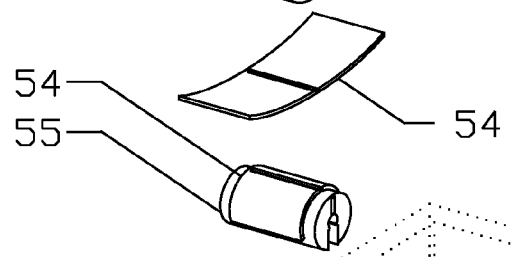
Figure 6D:
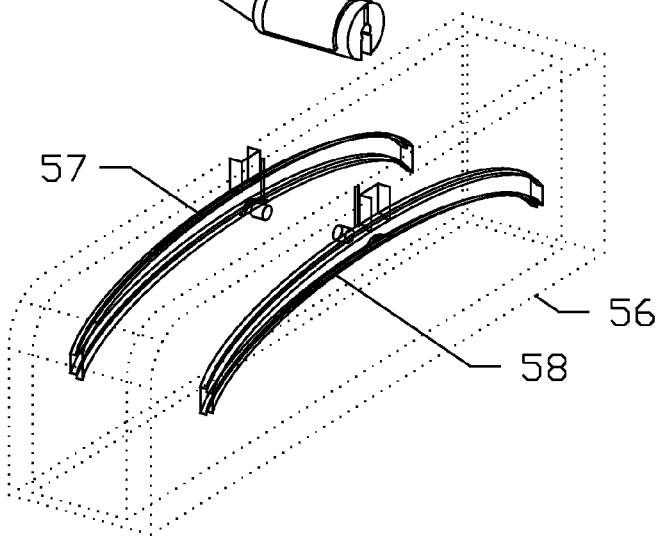

FIGS. 6A, 6B, 6C and 6D shows a schematic illustration of an example of a static pointing device applicator for a convex face of an ultrasound transducer: FIG. 6A shows the convex face 52 of the ultrasound transducer 51. FIG. 6B shows a pivotable rectangular enclosure 53. FIG. 6C shows a convex static pointing device 54 and a rotatable cylindrical drum 55 circumferentially wrapped by the convex static pointing device 54. FIG. 6D shows a see-through view of a box-shaped enclosure 56 with a pair of curvilinear guide rail slots 57 and 58 located on an outer surface of each vertical sidewall.

Figure 7A:
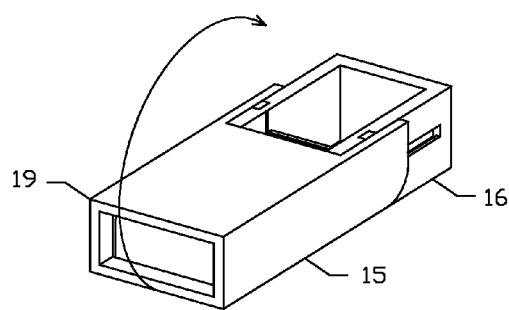
FIGS. 7A, 7B, 7C and 7D illustrate a schematic example of a sequence of a method of use of the static pointing device applicator.
Figure 7B:
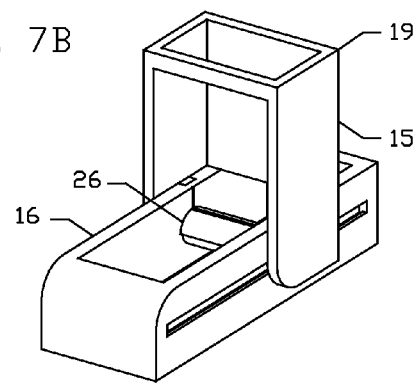
Figure 7C:
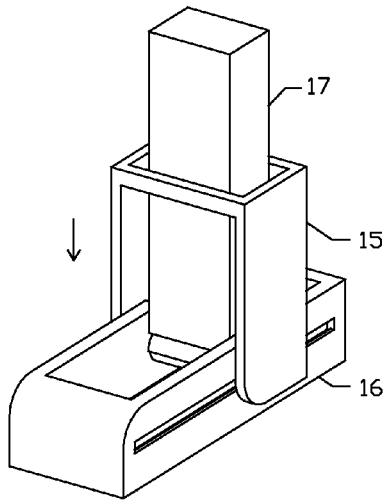
Figure 7D:
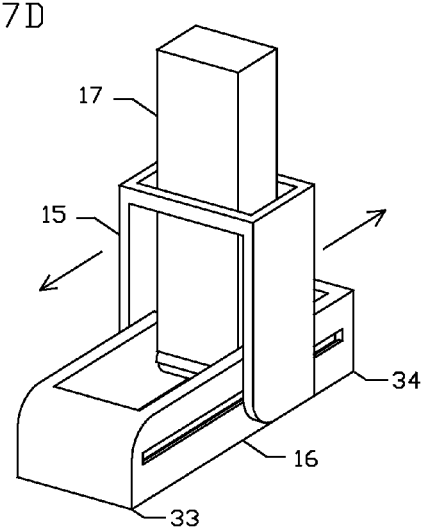

FIGS. 7A, 7B, 7C and 7D illustrate a schematic example of a sequence of a method of use of the static pointing device applicator. FIG. 7A shows the pivotable rectangular enclosure 15 folded up over the box-shaped enclosure 16. The pivotable rectangular enclosure 15 is pivotably unfolded to an erect position at a right angle to the box-shaped enclosure 16 by lifting up the proximal end 19. FIG. 7B shows the pivoted pivotable rectangular enclosure 15 at a right angle to the box-shaped enclosure 16, into which the flat ultrasound transducer head 17 is inserted toward the static pointing device 26 attached to the rotatable cylindrical drum. FIG. 7C shows a push-down movement of the pivotable rectangular enclosure 15 with the flat ultrasound transducer head 17 to get engaged in the longitudinal guide rail slots shown in FIG. 5. The push-down of the flat ultrasound transducer head 17 allows the ultrasound transducer head to contact with the static pointing device 26 with a downward pressure for secure attachment. FIG. 7D shows a horizontal to and fro movement of the pivotable rectangular enclosure 15 with the flat ultrasound transducer head 17 along the longitudinal guide rail slot of the box-shaped enclosure 16. The to and fro movement of the flat ultrasound transducer head 17 gliding over the static pointing device makes the static pointing device adhere to the flat face of the ultrasound transducer head 17 in a fail-safe and consistent way to assure of accuracy of the ultrasonographic positioning guide.

FIGS. 8A and 8B show a schematic example of a method of attaching the static pointing device to the convex face of the ultrasound transducer. FIG. 8A shows placement of the convex face 52 of the ultrasound transducer 51 in the pivotable rectangular enclosure 53 pivoted at a right angle to the box-shaped enclosure 56 having the curvilinear guide rail slots. One of the pair of the curvilinear guide rail slots is shown as 58. A push-down movement of the pivotable rectangular enclosure 53 with the ultrasound transducer 51 makes the pivotable rectangular enclosure 53 get engaged in the curvilinear guide rail slots and the convex face 52 of the ultrasound transducer head 51 contact with the static pointing device with a downward pressure. FIG. 8B shows a to and fro curvilinear movement of both the ultrasound transducer and pivotable rectangular enclosure along the curvilinear guide rail slots of the box-shaped enclosure in between the proximal and distal ends 59 and 60 of the box-shaped enclosure 56. The to and fro curvilinear movement of the ultrasound transducer face 52 gliding on the static pointing device makes the static pointing device adhere to the convex face of the convex ultrasound transducer in a fail-safe and consistent way to assure of accuracy of the ultrasonographic positioning guide.

It is to be understood that the aforementioned description of the static pointing device applicator and methods of use is simple illustrative embodiments of the principles of the present invention. Various modifications and variations of the description of the present invention are expected to occur to those skilled in the art without departing from the spirit and scope of the present invention. Therefore the present invention is to be defined not by the aforementioned description but instead by the spirit and scope of the following claims.

What is claimed is:

1. A static pointing device applicator, comprising:
   a box-shaped enclosure, a pivotable rectangular enclosure, a rotatable cylindrical drum and a non-reusable static pointing device;
   the box-shaped enclosure, provided in a plurality of mechanical configurations having an open upper part, a longitudinal guide rail slot on an outer surface of a longitudinal vertical sidewall and a pin protruding from an inner surface of the longitudinal vertical sidewall, which is enfoldedly assembled with the pivotable rectangular enclosure;
   the pivotable rectangular enclosure, provided in a rectangularly tubular configuration having an open proximal end, an open distal end and a wheel protruding from an inner surface of each longitudinal sidewall at the distal end, which is enfoldingly assembled with the box-shaped enclosure;

the rotatable cylindrical drum, provided in a cylindrical configuration having a central hole open to an open radially linear conduit disposed on each cylindrical end and a centering notch vertically disposed above said central hole, which is to be releasably inserted in a pair of the pins of the box-shaped enclosure and to rotate about said pins; and the non-reusable static pointing device, provided in a plurality of configurations as an ultrasound-transmissible flexible polymer sheet having an ultrasound-non-transmissible stationary linear pointer fixedly embedded in said flexible polymer sheet, which is to releasably wrap around an outer circumferential wall of the rotatable cylindrical drum and which has an adhesive surface contacting the face of the ultrasound transducer to be reversibly attached to the face of the ultrasound transducer.

2. The static pointing device applicator according to claim 1, wherein the box-shaped enclosure further comprises a linear centering recess located vertically above the pin on the inner surface of each longitudinal vertical sidewall, which reversibly mates with the centering notch of the rotatable cylindrical drum.

3. The static pointing device applicator according to claim 1, wherein the box-shaped enclosure is configured to releasably enclose a proximal portion of an ultrasound transducer through said open upper part, to let the pivotable rectangular enclosure pivot about said wheel and slide in said longitudinal guide rail slot and to releasably enclose and let the rotatable cylindrical drum rotate about said pin.

4. The static pointing device applicator according to claim 1, wherein the pivotable rectangular enclosure is configured to be reversibly folded up over the box-shaped enclosure and to be unfolded about said wheel of said distal end to a right angle to a longitudinal axis of the box-shaped enclosure, to let the proximal portion of the ultrasound transducer slide in and out from said open proximal end; and, in an unfolded configuration, to slide along the longitudinal axis of the box-shaped enclosure back and forth by way of a pair of the wheels of the distal end rotating inside the longitudinal guide rail slots of the box-shaped enclosure.

5. The static pointing device applicator according to claim 4, wherein a central transverse axial line of the distal end of the pivotable rectangular enclosure in the unfolded configuration at the right angle to the box-shaped enclosure is configured to align with the central longitudinal axial line located on the outer circumferential wall of the rotatable cylindrical drum.

6. The static pointing device applicator according to claim 1, wherein the rotatable cylindrical drum is configured to be releasably wrapped around on the outer circumferential wall of said rotatable cylindrical drum by the non-reusable static pointing device and to deliver the non-reusable static pointing device to the face of the ultrasound transducer enclosed in the pivotable rectangular enclosure by rotatably contacting with the face of the ultrasound transducer.

7. The static pointing device applicator according to claim 1, wherein the non-reusable static pointing device is configured to be flexible to conform to a contour of the face of the ultrasound transducer.

8. The static pointing device applicator according to claim 1, wherein the longitudinal guide rail slot of the outer surface of each longitudinal vertical sidewall of the box-shaped enclosure is coupled with the wheel protruding from the inner surface of the distal end of the pivotable rectangular enclosure, in which the wheel rotates along the longitudinal axis of the box-shaped enclosure.

9. The static pointing device applicator according to claim 1, wherein the at least one configuration of the longitudinal guide rail slot of the longitudinal vertical sidewall of the box-shaped enclosure is linear along the longitudinal axis of the box-shaped enclosure, which is to let a flat face of an ultrasound transducer glide on the non-reusable static pointing device wrapped around the rotatable cylindrical drum.

10. The static pointing device applicator according to claim 1, wherein the at least one configuration of the longitudinal guide rail slot of the longitudinal vertical sidewall of the box-shaped enclosure is curvilinear along the longitudinal axis of the box-shaped enclosure with a convex portion of the curvilinear longitudinal guide rail slot pointing to a convex face of an ultrasound transducer, which is to let the convex face of the ultrasound transducer glide on the non-reusable static pointing device wrapped around the rotatable cylindrical drum.

11. The static pointing device applicator according to claim 1, wherein the at least one configuration of the ultrasound-non-transmissible stationary linear pointer has said ultrasound-non-transmissible stationary linear pointer embedded in the non-reusable static pointing device in a way to be positioned along a central longitudinal axial line of the rotatable cylindrical drum.

12. The static pointing device applicator according to claim 1, wherein the at least one configuration of the ultrasound-non-transmissible stationary linear pointer has said ultrasound-non-transmissible stationary linear pointer embedded in the non-reusable static pointing device in a way to circumferentially wrap around the outer circumferential wall of the rotatable cylindrical drum at a right angle to the central longitudinal axial line of the rotatable cylindrical drum.

* * * * *